(12) United States Patent
Watanabe et al.

(10) Patent No.: US 9,339,629 B2
(45) Date of Patent: May 17, 2016

(54) CATHETER

(71) Applicant: ASAHI INTECC CO., LTD., Nagoya-shi, Aichi (JP)

(72) Inventors: Nobuyoshi Watanabe, Kasugai (JP); Takayuki Yagi, Seto (JP)

(73) Assignee: ASAHI INTECC CO., LTD., Nagoya-shi (JP)

( * ) Notice: Subject to any disclaimer, the term of this patent is extended or adjusted under 35 U.S.C. 154(b) by 0 days.

(21) Appl. No.: 14/661,481

(22) Filed: Mar. 18, 2015

(65) Prior Publication Data
US 2015/0273182 A1 Oct. 1, 2015

(30) Foreign Application Priority Data
Mar. 25, 2014 (JP) ................................. 2014-062106

(51) Int. Cl.
*A61M 25/00* (2006.01)

(52) U.S. Cl.
CPC ........... *A61M 25/008* (2013.01); *A61M 25/005* (2013.01); *A61M 25/0053* (2013.01); *A61M 25/0069* (2013.01)

(58) Field of Classification Search
CPC .......... A61M 25/005; A61M 25/0012; A61M 25/0069
USPC ................................................ 604/526, 527
See application file for complete search history.

(56) References Cited

U.S. PATENT DOCUMENTS

| 4,921,483 | A | * | 5/1990 | Wijay | A61M 25/1002 |
| | | | | | 604/102.02 |
| 5,156,595 | A | * | 10/1992 | Adams | A61M 25/1027 |
| | | | | | 604/913 |
| 5,449,343 | A | * | 9/1995 | Samson | A61M 25/09 |
| | | | | | 604/103.1 |
| 5,769,830 | A | | 6/1998 | Parker | |
| 6,824,553 | B1 | * | 11/2004 | Samson | A61M 25/005 |
| | | | | | 606/192 |
| 7,909,779 | B2 | | 3/2011 | Shimogami et al. | |
| 2004/0092867 | A1 | * | 5/2004 | Murray, III | A61M 25/104 |
| | | | | | 604/103 |
| 2007/0260224 | A1 | * | 11/2007 | Von Oepen | A61M 25/0054 |
| | | | | | 604/528 |
| 2007/0270780 | A1 | * | 11/2007 | Venturelli | A61F 2/95 |
| | | | | | 604/526 |

(Continued)

FOREIGN PATENT DOCUMENTS

| EP | 1674124 A1 | 6/2006 |
| EP | 2174685 A1 | 4/2010 |

(Continued)

OTHER PUBLICATIONS

Sep. 17, 2015 Search Report issued in European Application No. 15159943.8.

*Primary Examiner* — Gerald Landry, II
(74) *Attorney, Agent, or Firm* — OLiff PLC

(57) ABSTRACT

A catheter includes a main body and a distal end tip. The main body includes an inner layer having a first lumen, a coil body wound around an outer periphery of the inner layer and made of a metal, and an outer layer that covers an outer periphery of the coil body. The distal end tip is made of metal and has a second lumen that communicates with the first lumen. The distal end tip is provided at a distal end of the main body, and is bonded to a distal end of the coil body and is bonded to an inner peripheral surface of a distal end portion of the coil body.

21 Claims, 5 Drawing Sheets

(56) References Cited

U.S. PATENT DOCUMENTS

| | | | | |
|---|---|---|---|---|
| 2008/0088230 | A1* | 4/2008 | Suzuri | C09K 11/06 313/504 |
| 2008/0097248 | A1* | 4/2008 | Munoz | A61M 25/0009 600/585 |
| 2009/0018525 | A1* | 1/2009 | Waite | A61M 25/005 604/508 |
| 2010/0094258 | A1* | 4/2010 | Shimogami | A61M 25/005 604/527 |
| 2012/0271232 | A1* | 10/2012 | Katsurada | A61M 25/0052 604/103.09 |
| 2012/0310213 | A1* | 12/2012 | Kronfeld | A61M 25/0012 604/526 |
| 2014/0236279 | A1* | 8/2014 | Dillon | A61F 2/966 623/1.12 |
| 2014/0257460 | A1* | 9/2014 | Gibbons, Jr. | A61F 2/966 623/1.12 |

FOREIGN PATENT DOCUMENTS

| | | |
|---|---|---|
| JP | 2007244492 A | 9/2007 |
| JP | 4693091 B2 | 6/2011 |
| WO | 2011/033783 A1 | 3/2011 |

\* cited by examiner

CATHETER

CROSS REFERENCE TO RELATED APPLICATION

This application claims priority to Japanese Patent Application No. 2014-062106 filed in the Japan Patent Office on Mar. 25, 2014, the entire contents of which are incorporated herein by reference.

BACKGROUND

The disclosed embodiments relate to a catheter that can be inserted into a hard stenosis or a bone.

Therapeutic catheters that are inserted into hard stenoses (for example, calcified stenoses) formed in blood vessels, bile ducts, pancreatic ducts, etc., and bone-marrow-sucking catheters that are inserted into bones to suck bone marrow are generally provided with distal end tips made of a rigid metal. The distal end tips are attached to the distal ends of catheter shafts so that the catheters can be inserted into the hard stenoses and bones (see, for example, Japanese Unexamined Patent Application Publication No. 2007-244492).

In the catheter according to Japanese Unexamined Patent Application Publication No. 2007-244492, an outer layer of the catheter is removed to expose a braid, and a distal end tip made of a metal is bonded to the braid, so that the distal end tip is bonded to a catheter shaft with sufficient bonding strength.

SUMMARY

However, in the catheter according to Japanese Unexamined Patent Application Publication No. 2007-244492, since the distal end tip made of a metal is bonded to an outer peripheral surface of the braid, the outer diameter of the distal end tip is larger than the outer diameter of the catheter shaft. Therefore, the insertion performance of the catheter that is inserted into a hard stenosis or a bone is degraded. In addition, in the case where a hard stenosis is formed at an end of a blood vessel, a bile duct, a pancreatic duct, or the like, the catheter inserted into the blood vessel, bile duct, pancreatic duct, or the like is greatly bent. Therefore, load is concentrated at a bonding portion between the proximal end of the distal end tip and the braid. When the catheter is rotated in this state, there is a risk that the proximal end of the distal end tip made of a metal will be partially separated from the braid. In particular, when the catheter is rotated while the catheter is greatly bent and the distal end tip is caught on the hard stenosis or bone, there is a risk that the proximal end of the distal end tip made of a metal will be separated from the braid due to the load concentrated at the bonding portion between the proximal end of the distal end tip and the braid. The proximal end of the distal end tip that has been separated from the braid may break through the outer layer and damage a normal portion of the blood vessel, bile duct, pancreatic duct, or the like. There is also a risk that the distal end tip itself will break off from the catheter shaft and be left in the blood vessel, bile duct, pancreatic duct, or the like.

In light of the above-described circumstances, it is an object of the disclosed embodiments to provide a catheter in which a distal end tip made of a metal is bonded to a distal end of a coil body and to an inner peripheral surface of a distal end portion of the coil body so that sufficient bonding strength can be provided between the distal end tip and the coil body without making the outer diameter of the distal end tip larger than the outer diameter of the catheter shaft.

According to an aspect of at least some embodiments, a catheter includes a main body and a distal end tip. The main body includes an inner layer having a first lumen, a coil body wound around an outer periphery of the inner layer and made of a metal, and an outer layer that covers an outer periphery of the coil body. The distal end tip is made of a metal and has a second lumen that communicates with the first lumen, the distal end tip being provided at a distal end of the main body. The distal end tip is bonded to a distal end of the coil body and is bonded to an inner peripheral surface of a distal end portion of the coil body.

With a catheter having the above structure, the distal end tip made of a metal is bonded to the distal end of the coil body and is bonded to the inner peripheral surface of the distal end portion of the coil body. Therefore, sufficient bonding strength can be provided between the distal end tip and the coil body without making the outer diameter of the distal end tip larger than the outer diameter of the catheter shaft. As a result, the insertion performance of the catheter that is inserted into a hard stenosis or a bone can be improved. In addition, since the distal end tip made of a metal is bonded to the inner peripheral surface of the coil body in addition to being bonded to the distal end of the coil body, the risk that the distal end tip itself will break off from the catheter shaft is reduced.

DETAILED DESCRIPTION OF EMBODIMENTS

Figure 1:
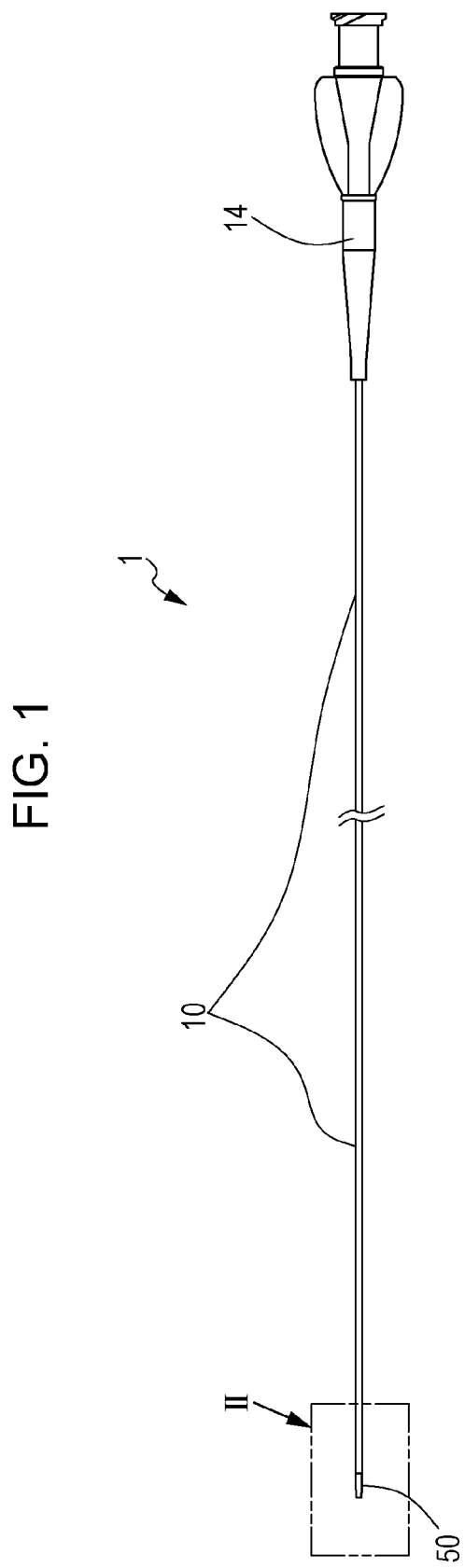
FIG. 1 illustrates the overall structure of a catheter according to the disclosed embodiments.
Figure 2:
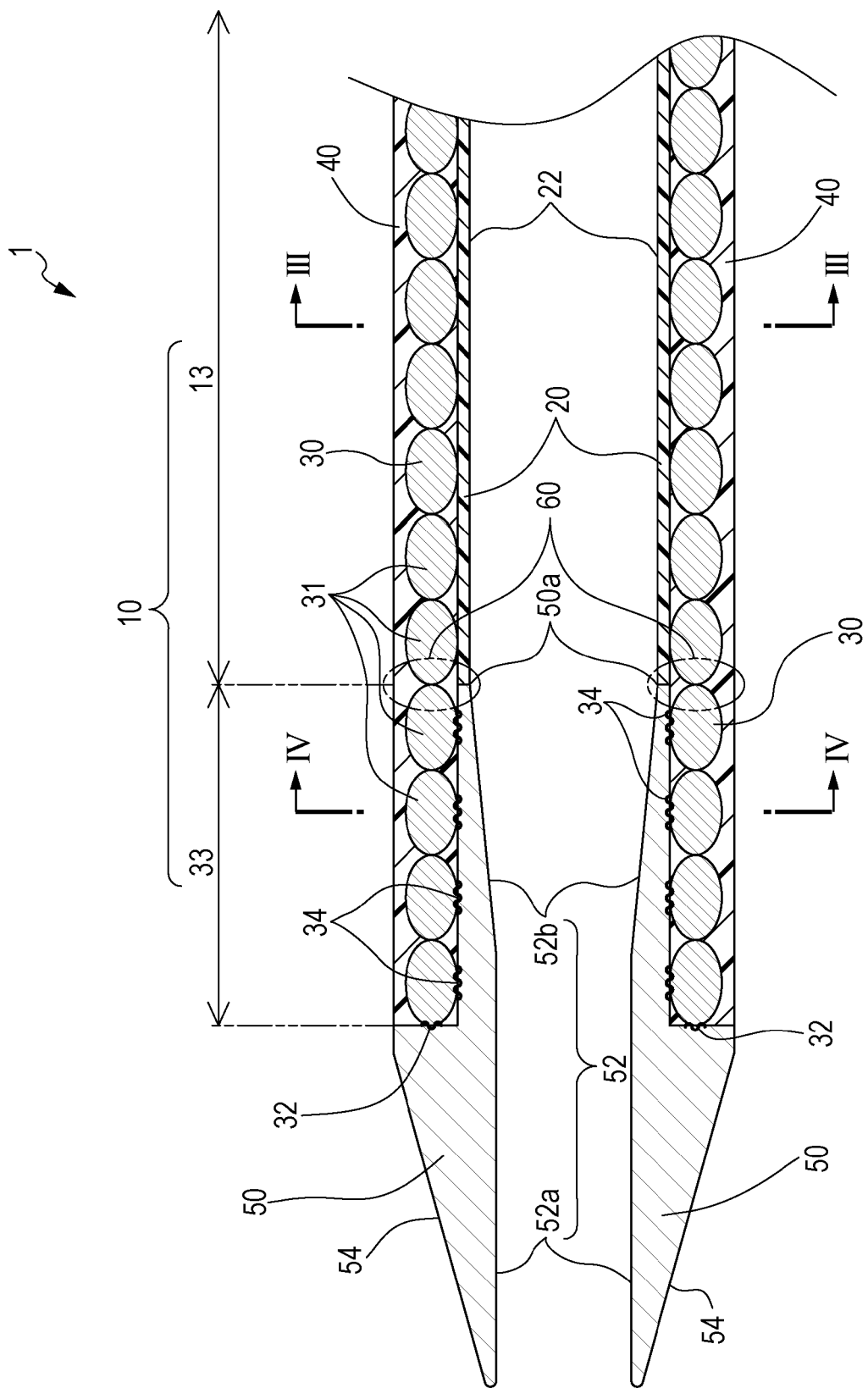
FIG. 2 is an enlarged view of part II illustrated in FIG. 1.

A catheter 1 according to disclosed embodiments will be described with reference to FIGS. 1 to 4. In FIGS. 1 and 2, a distal end of the catheter 1 that is inserted into a body is at the left side, and a proximal end of the catheter 1 that is manipulated by an operator, such as a doctor, is at the right side.

The catheter 1 is used, for example, to treat a stenosis in a blood vessel of the heart, a bile duct, or a pancreatic duct, or to suck bone marrow from a bone. As illustrated in FIG. 1, the catheter 1 mainly includes a catheter shaft 10, a connector 14 attached to the proximal end of the catheter shaft 10, and a distal end tip 50 made of a metal that is attached to the distal end of the catheter shaft 10.

As illustrated in FIG. 2, which is an enlarged view of part II in FIG. 1, the catheter shaft 10 includes a main body 13 and a distal end portion 33. The main body 13 of the catheter shaft 10 includes an inner layer 20, a coil body 30 that serves as a reinforcing member, and an outer layer 40.

The inner layer 20 is made of a resin, and forms a lumen 22 that allows a guidewire or another catheter to be inserted therethrough. The resin material of the inner layer 20 is not particularly limited. However, considering the slidability of the guidewire and another catheter inserted through the lumen 22, polytetrafluoroethylene (PTFE) is preferably used as the resin material of the inner layer 20.

The coil body 30 made of a metal is wound around the outer periphery of the inner layer 20. The coil body 30 includes wires 31. Each wire 31 may either be a single wire or a stranded wire formed by twisting a plurality of wires together. Considering the rotating force of the catheter 1, the wires 31 included in the coil body 30 are preferably stranded wires. The metal material of the wires 31 is not particularly limited, and a stainless steel (SUS304, SUS316, etc.), gold, platinum, tungsten, nickel, or an alloy thereof may be used.

The outer periphery of the coil body 30 is covered with the outer layer 40 made of a resin. The resin material of the outer layer 40 is not particularly limited, and polyamide, polyamide elastomer, polyester, polyurethane, etc., may be used.

The distal end tip 50 made of a metal is attached to the distal end of the catheter shaft 10. The distal end tip 50 includes an outer peripheral surface 54 that is tapered such that the diameter thereof decreases toward the distal end, and a lumen 52 that communicates with the lumen 22 of the inner layer 20 and that allows a guidewire or another catheter to be inserted therethrough. As described below, the lumen 52 includes a straight portion 52a that has a substantially constant inner diameter and a tapered portion 52b that has an inner diameter that increases toward the proximal end as the thickness of the distal end tip 50 decreases toward the proximal end. The metal material of the distal end tip 50 is not particularly limited, and a stainless steel (SUS304, SUS316, etc.), gold, platinum, tungsten, nickel, or an alloy thereof may be used. At least one of the distal end tip 50 and the coil body 30 is preferably made of a radiopaque metal material so that the position of the distal end of the catheter 1 can be determined in a radiographic image.

Figure 3:
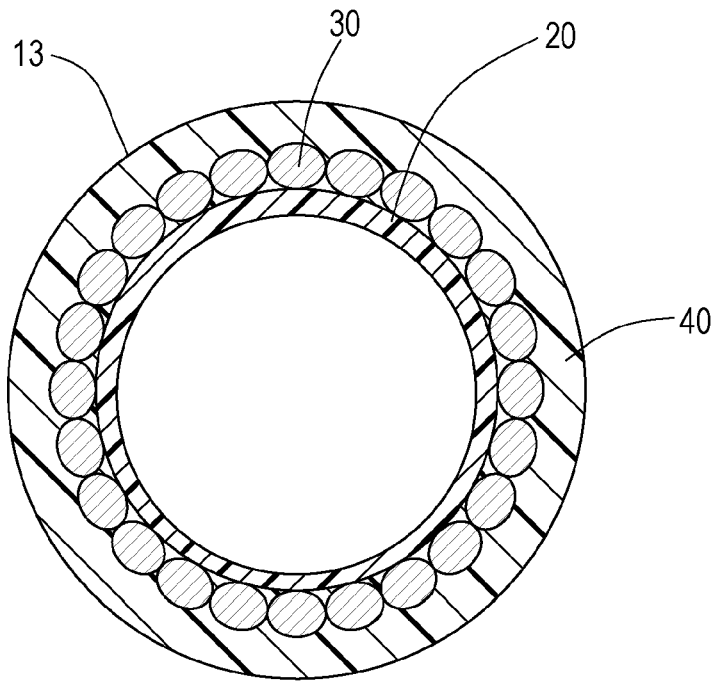
FIG. 3 is a sectional view of FIG. 2 taken along line III-III.

FIG. 3 is a sectional view of FIG. 2 taken along line III-III. As illustrated in FIG. 3, the main body 13 of the catheter shaft 10 includes the inner layer 20, the coil body 30, and the outer layer 40 arranged in that order in the radial direction.

Figure 4:
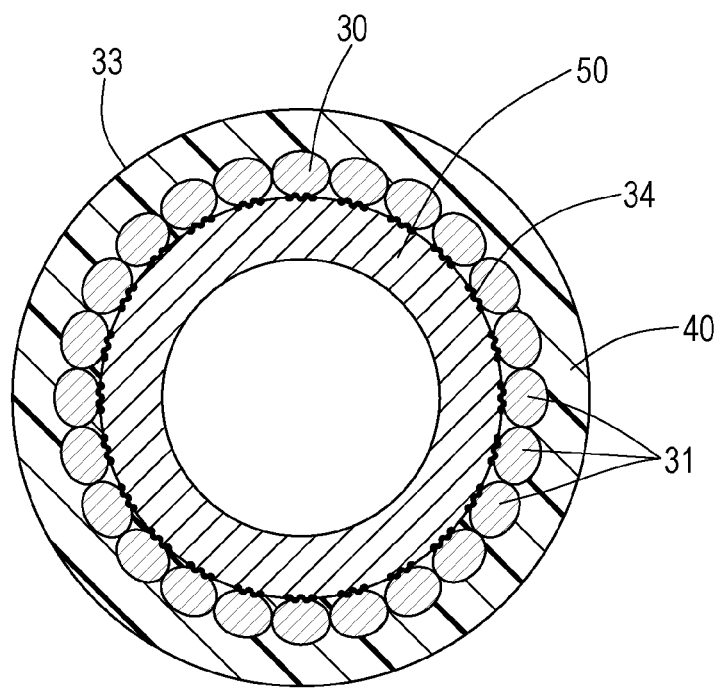
FIG. 4 is a sectional view of FIG. 2 taken along line IV-IV.

FIG. 4 is a sectional view of FIG. 2 taken along line IV-IV. As illustrated in FIG. 4, the distal end portion 33 of the catheter shaft 10 includes the distal end tip 50, the coil body 30, and the outer layer 40 arranged in that order in the radial direction.

In the distal end portion 33 of the catheter shaft 10, the distal end tip 50 is bonded to a distal end 32 of the coil body 30 and is bonded to an inner peripheral surface 34 of the coil body 30 (see FIGS. 2 and 4). The length of the distal end portion 33 of the catheter shaft 10 can be adjusted as appropriate. In FIG. 2, the length of the distal end portion 33 of the catheter shaft 10 (in other words, the length of a portion of the coil body 30 that is bonded to the distal end tip 50) corresponds to four wires 31 of the coil body 30 (more precisely, four windings or revolutions of the wire 31 forming the coil body 30). In the case where the bonding strength between the distal end tip 50 and the coil body 30 needs to be increased, the length of the distal end portion 33 may be increased to, for example, a length corresponding to six wires 31 of the coil body 30. In the case where the bonding strength between the distal end tip 50 and the coil body 30 is sufficient, the length of the distal end portion 33 may be reduced.

As described above, with the catheter 1, the length of the distal end portion 33 of the catheter shaft 10 to which the distal end tip 50 is bonded can be adjusted to any length. Therefore, sufficient bonding strength can be provided between the distal end tip 50 and the coil body 30 without making the outer diameter of the distal end tip 50 greater than the outer diameter of the catheter shaft 10. As a result, the insertion performance of the catheter 1 that is inserted into a hard stenosis or a bone can be improved. In addition, since the distal end tip 50 made of a metal is bonded not only to the distal end 32 of the coil body 30 but also to the inner peripheral surface 34 of the coil body 30, the risk that the distal end tip 50 itself will break off from the catheter shaft 10 can be reduced.

As illustrated in FIG. 2, in the distal end portion 33 of the catheter shaft 10, the distal end tip 50, which is bonded to the inner peripheral surface 34 of the coil body 30, includes the tapered portion 52b having a thickness that decreases toward the proximal end 50a of the distal end tip 50 so that the thickness is at a minimum at the proximal end 50a. Thus, in the distal end portion 33 of the catheter shaft 10, the rigidity of the distal end tip 50 gradually increases from the proximal end 50a toward the distal end. Therefore, even when the catheter 1 is rotated while the catheter 1 is greatly bent and the distal end tip 50 is caught on a hard stenosis or bone, concentration of load does not easily occur at a boundary 60 between the proximal end 50a of the distal end tip 50 and the coil body 30. Accordingly, the risk that the distal end tip 50 will be separated from the coil body 30 can be further reduced. As a result, the risk that the distal end tip 50 itself will break off from the catheter shaft 10 can be reduced.

Figure 5:
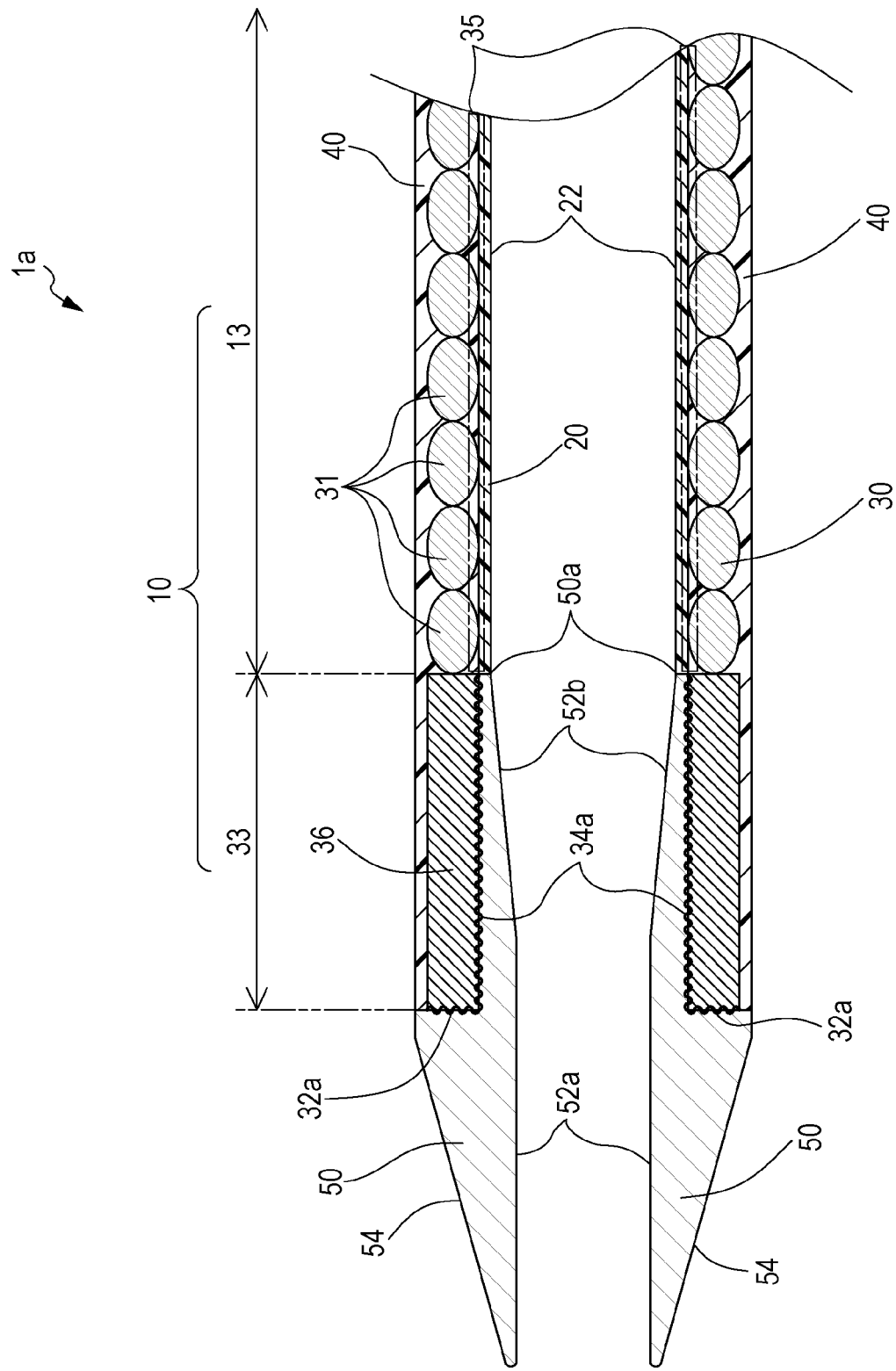
FIG. 5 is an enlarged view of a catheter according to the disclosed embodiments.

Next, a catheter 1a according to the disclosed embodiments will be described with reference to FIG. 5. Similar to FIGS. 1 and 2, in FIG. 5, a distal end of the catheter 1a that is inserted into a body is at the left side, and a proximal end of the catheter 1a that is manipulated by an operator, such as a doctor, is at the right side.

Only the difference from the catheter 1 illustrated in FIG. 2 will be described. As illustrated in FIG. 5, in the catheter 1a, a distal end portion 33 of a catheter shaft 10 includes a bonding portion 36 in which the wires 31 included in a coil body 30 are bonded together. The bonding portion 36 is formed by melting the wires 31 included in the coil body 30 with a laser or the like. A distal end tip 50 is bonded to a distal end 32a of the bonding portion 36 and is bonded to an inner peripheral surface 34a of the bonding portion 36. When the bonding portion 36 is formed by bonding the wires 31 included in the coil body 30 together, movement of the wires 31 included in the coil body 30 is restricted in the distal end portion 33 of the catheter shaft 10. Therefore, the distal end tip 50 and the coil body 30 can be easily and reliably bonded together.

In addition, in the catheter 1a, the inner peripheral surface 34a of the bonding portion 36 is flatter than an inner peripheral surface 35 of the coil body 30 in a main body 13 of the catheter shaft 10 (in other words, the inner peripheral surface 35 of a portion of the coil body 30 that is not bonded to the distal end tip 50). Since the inner peripheral surface 34a of the bonding portion 36 is flat, the bonding area between the distal end tip 50 and the coil body 30 can be increased, and the risk that the distal end tip 50 will be separated from the coil body 30 can be reduced. As a result, the risk that the distal end tip 50 itself will break off from the catheter shaft 10 can be reduced.

Figure 6:
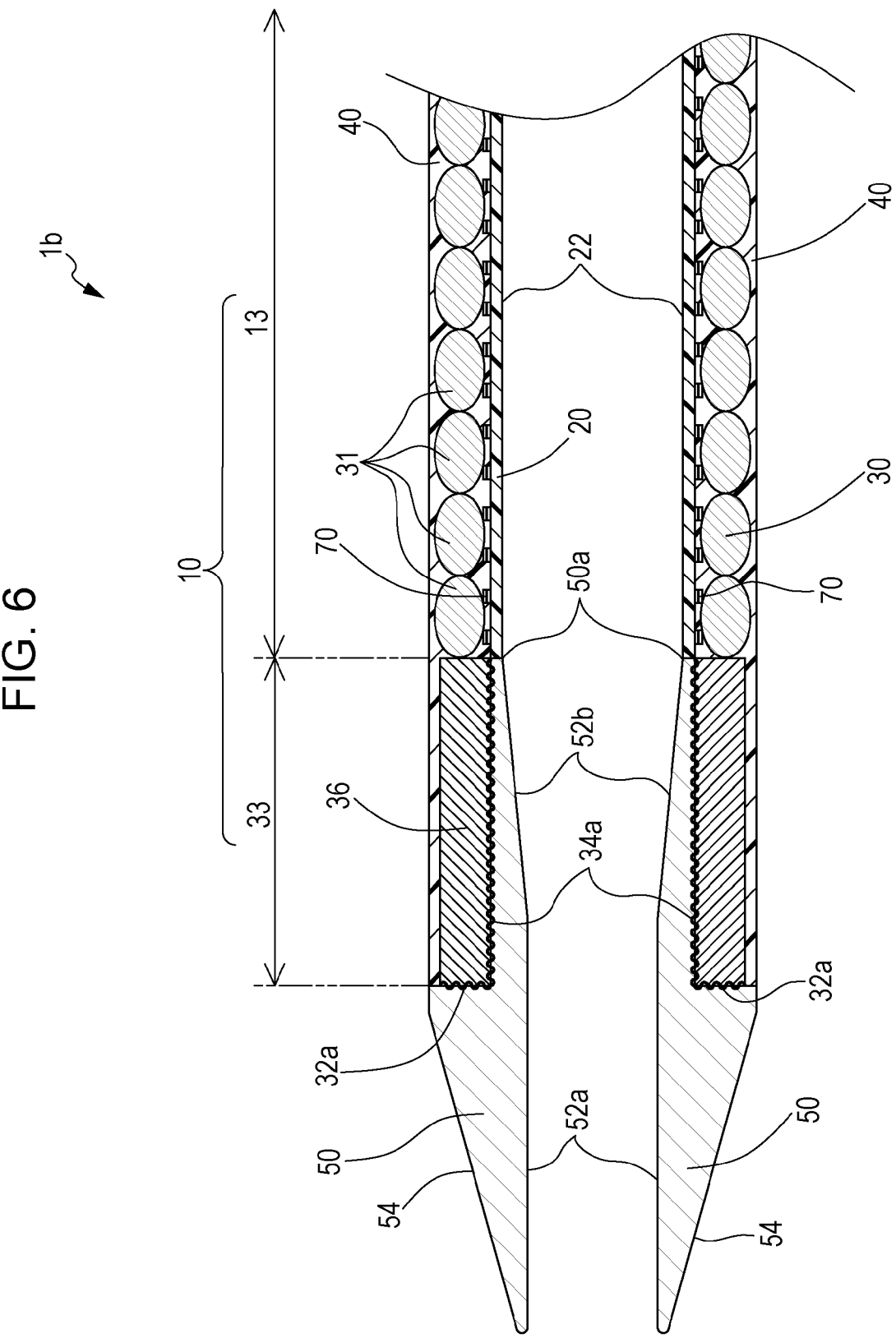
FIG. 6 is an enlarged view of a catheter according to the disclosed embodiments.

Next, a catheter 1b according to the disclosed embodiments will be described with reference to FIG. 6. Similar to FIGS. 1, 2, and 5, in FIG. 6, a distal end of the catheter 1b that is inserted into a body is at the left side, and a proximal end of the catheter 1b that is manipulated by an operator, such as a doctor, is at the right side.

Only the difference from the catheter 1a illustrated in FIG. 5 will be described. As illustrated in FIG. 6, the catheter 1b includes a catheter shaft 10 including a main body 13 in which a braid 70 is embedded between an inner layer 20 and a coil body 30 so as to extend in the longitudinal direction. Thus, the rigidity of the main body 13 of the catheter shaft 10 can be increased, and the pushing force applied in a direction toward the distal end by the operator can be more easily transmitted to a distal end tip 50. In addition, although not illustrated in FIG. 6, a proximal end 50*a* of the distal end tip 50 may be bonded not only to the coil body 30 but also to the braid 70. In such a case, the risk that the distal end tip 50 will be separated from the coil body 30 and the braid 70 can be reduced. As a result, the risk that the distal end tip 50 itself will break off from the catheter shaft 10 can be further reduced.

As described above, in the catheters 1, 1*a*, and 1*b*, the distal end tip 50 is attached to the distal end 32, 32*a* of the coil body 30 and is attached to the inner peripheral surface 34, 34*a* of the coil body 30. Therefore, sufficient bonding strength can be provided between the distal end tip 50 and the coil body 30 without making the outer diameter of the distal end tip 50 larger than the outer diameter of the catheter shaft 10. As a result, the insertion performance of the catheter 1 that is inserted into a hard stenosis or a bone can be improved. In addition, the risk that the distal end tip 50 itself will break off from the catheter shaft 10 can be reduced.

What is claimed is:

1. A catheter comprising:
   a main body including an inner layer having a first lumen, a coil body wound around an outer periphery of the inner layer and made of metal, and an outer layer that covers an outer periphery of the coil body; and
   a distal end tip made of metal, the distal end tip having a second lumen that communicates with the first lumen, the distal end tip being provided at a distal end of the main body,
   wherein the distal end tip is bonded to a distal end of the coil body and the distal end tip is bonded to an interior peripheral surface of a distal end portion of the coil body.

2. The catheter according to claim 1, wherein, in the distal end portion of the coil body, windings of wire included in the coil body are bonded together, and the interior peripheral surface of the distal end portion of the coil body is flatter than an interior peripheral surface of a portion of the coil body that is not bonded to the distal end tip.

3. The catheter according to claim 1, wherein a portion of the distal end tip that is bonded to the interior peripheral surface of the distal end portion of the coil body is tapered such that a thickness of the portion of the distal end tip decreases toward a proximal end of the distal end tip.

4. The catheter according to claim 3, wherein a diameter of the second lumen increases toward the proximal end of the distal end tip in the portion of the distal end tip that is tapered.

5. The catheter according to claim 2, wherein a portion of the distal end tip that is bonded to the interior peripheral surface of the distal end portion of the coil body is tapered such that a thickness of the portion of the distal end tip decreases toward a proximal end of the distal end tip.

6. The catheter according to claim 5, wherein a diameter of the second lumen increases toward the proximal end of the distal end tip in the portion of the distal end tip that is tapered.

7. The catheter according to claim 1, wherein an outer diameter of the distal end tip is no larger than an outer diameter of a distal-most end portion of the main body.

8. The catheter according to claim 1, wherein a distal end of the inner layer abuts a proximal end of the distal end tip.

9. The catheter according to claim 1, wherein the coil body and the outer layer extend distally beyond a distal end of the inner layer.

10. The catheter according to claim 1, wherein a radially outer surface of the distal end tip includes a shoulder defining first and second surfaces, the first surface facing proximally and bonded to the distal end of the coil body, the second surface facing radially outward and bonded to the interior peripheral surface of the distal end portion of the coil body.

11. A catheter comprising:
    a main body including an inner layer having a first lumen, a coil body wound around an outer periphery of the inner layer and made of metal, and an outer layer that covers an outer periphery of the coil body; and
    a distal end tip made of metal, the distal end tip having a second lumen that communicates with the first lumen, the distal end tip being provided at a distal end of the main body, an outer surface of the distal end tip having a first surface that faces proximally and that is bonded to a distal end of the coil body, the outer surface of the distal end tip having a second surface that faces radially outward and that is bonded to an interior peripheral surface of a distal end portion of the coil body.

12. The catheter according to claim 11, wherein, in the distal end portion of the coil body, windings of wire included in the coil body are bonded together, and the interior peripheral surface of the distal end portion of the coil body is flatter than an interior peripheral surface of a portion of the coil body that is not bonded to the distal end tip.

13. The catheter according to claim 11, wherein a portion of the distal end tip that is bonded to the interior peripheral surface of the distal end portion of the coil body is tapered such that a thickness of the portion of the distal end tip decreases toward a proximal end of the distal end tip.

14. The catheter according to claim 13, wherein a diameter of the second lumen increases toward the proximal end of the distal end tip in the portion of the distal end tip that is tapered.

15. The catheter according to claim 12, wherein a portion of the distal end tip that is bonded to the interior peripheral surface of the distal end portion of the coil body is tapered such that a thickness of the portion of the distal end tip decreases toward a proximal end of the distal end tip.

16. The catheter according to claim 15, wherein a diameter of the second lumen increases toward the proximal end of the distal end tip in the portion of the distal end tip that is tapered.

17. The catheter according to claim 11, wherein an outer diameter of the distal end tip is no larger than an outer diameter of a distal-most end portion of the main body.

18. The catheter according to claim 11, wherein a distal end of the inner layer abuts a proximal end of the distal end tip.

19. The catheter according to claim 11, wherein the coil body and the outer layer extend distally beyond a distal end of the inner layer.

20. The catheter according to claim 1, wherein the distal end tip is directly bonded to the interior peripheral surface of the distal end portion of the coil body.

21. The catheter according to claim 11, wherein the second surface of the distal end tip is directly bonded to the interior peripheral surface of the distal end portion of the coil body.

* * * * *